(12) United States Patent
Kornblith

(10) Patent No.: US 6,900,027 B1
(45) Date of Patent: *May 31, 2005

(54) METHOD FOR PREPARING CELL CULTURES FROM BIOLOGICAL SPECIMENS FOR CHEMOTHERAPEUTIC AND OTHER ASSAYS

(75) Inventor: Paul L. Kornblith, Pittsburgh, PA (US)

(73) Assignee: Precision Therapeutics, Inc., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/040,161

(22) Filed: Mar. 17, 1998

Related U.S. Application Data

(63) Continuation of application No. 08/679,056, filed on Jul. 12, 1996, now Pat. No. 5,728,541.

(51) Int. Cl.$^7$ .................................................. C12Q 1/02
(52) U.S. Cl. ............................. 435/29; 435/30; 435/32; 435/261
(58) Field of Search ............................. 435/2, 29, 30, 435/32, 240.2, 261, 803

(56) References Cited

U.S. PATENT DOCUMENTS

| | | | |
|---|---|---|---|
| 4,423,145 A | 12/1983 | Stampfer et al. | 435/32 |
| 4,559,299 A | 12/1985 | Rotman | |
| 4,668,618 A | 5/1987 | Thornthwaite | 435/6 |
| 4,816,395 A | 3/1989 | Hancock et al. | |
| 4,937,187 A | 6/1990 | Rotman | 435/30 |
| 4,996,145 A | 2/1991 | Weisenthal | |
| 5,242,806 A | 9/1993 | Yen-Maguire et al. | 435/32 |
| 5,270,172 A | 12/1993 | Morgan | 435/29 |
| 5,403,574 A | 4/1995 | Piwnica-Worms | |
| 5,443,950 A | 8/1995 | Naughton et al. | 435/1 |
| 5,607,918 A | 3/1997 | Eriksson et al. | 514/12 |
| 5,705,270 A | 1/1998 | Soon-Shiong et al. | |
| 5,728,541 A * | 3/1998 | Kornblith | 435/29 |
| 5,789,158 A | 8/1998 | Knowles et al. | 435/6 |
| 5,874,218 A | 2/1999 | Drolet et al. | 435/6 |
| 5,888,765 A | 3/1999 | Patterson et al. | 435/69.1 |
| 5,942,385 A | 8/1999 | Hirth | 435/4 |
| 5,972,639 A | 10/1999 | Parandoosh | 435/29 |
| 6,008,007 A | 12/1999 | Fruehauf et al. | |
| 6,020,473 A | 2/2000 | Keyt et al. | 536/23.1 |
| 6,111,092 A | 8/2000 | Williamson | |
| 6,261,795 B1 | 7/2001 | Fruehauf et al. | |
| 6,303,324 B1 | 10/2001 | Fruehauf et al. | |
| 6,335,170 B1 | 1/2002 | Orntoft | 435/6 |
| 6,416,967 B2 | 7/2002 | Kornblith | 435/29 |
| 6,511,806 B1 | 1/2003 | Fruehauf et al. | |
| 6,664,062 B1 | 12/2003 | Stanton | |
| 2002/0168679 A1 | 11/2002 | Naus et al. | |
| 2002/0192638 A1 | 12/2002 | Kornblith | |
| 2003/0096290 A1 | 5/2003 | Fruehauf et al. | |
| 2004/0023375 A1 | 2/2004 | Kornblith et al. | |
| 2004/0072722 A1 | 4/2004 | Kornblith et al. | |
| 2004/0086888 A1 | 5/2004 | Kornblith et al. | |

FOREIGN PATENT DOCUMENTS

| | | |
|---|---|---|
| WO | WO 96/10742 | 4/1996 |
| WO | WO98/02038 | 1/1998 |
| WO | WO02/33117 A2 | 4/2002 |
| WO | WO2004/015065 A2 | 2/2004 |
| WO | WO2004035833 A1 | 4/2004 |

OTHER PUBLICATIONS

"Evaluation of Chemopreventive Agents in Different Mechanistic Classes Using a Rat Tracheal Epithelial Cell Culture Transformation Assay." Arnold et al., Cancer Research. vol. 55. pp. 537–543 (1995).

"Evidence of a Direct Relationship Between the Increase in the In Vitro Passage Number of Human Non–Small–Cell–Lung Cancer Primocultures and Their Chemosensitivity." Kruczynski et al., Anticancer Research. vol. 13, pp. 507–514 (1993).

Alley, M., "Morphometric and Colorimetric Analyses of Human Tumor Cell Line Growth and Drug Sensitivity in Soft Agar Culture," Cancer Research, vol. 51, pp. 1247–1256 (1991).

Andreotti, P., "TCA–100 Tumour Chemosensitivity Assay: Differences in Sensitivity between Cultured Tumour Cell Lines and Clinical Studies," J Biolumin Chemilumin, vol. 9, pp. 373–378 (1994).

Broadley, C., et al., "A Tissue–Culture Model for the Study of Canine Vocal Fold Fibroblasts," Laryngoscope, vol. 105, No. 1, pp. 23–27 (1995).

Burczynski, M., et al., "Toxicogenomics–Based Discrimination of Toxic Mechanism in HepG2 Human Hepatoma Cells," Toxicological Sciences, vol. 58, No. 2, pp. 399–415 (2000).

(Continued)

*Primary Examiner*—Ralph Gitomer
(74) *Attorney, Agent, or Firm*—Morgan, Lewis & Bockius, LLP

(57) ABSTRACT

An improved system for screening a multiple of candidate therapeutic or chemotherapeutic agents for efficacy as to a specific patient, in which a tissue sample from the patient is harvested, cultured and separately exposed to a plurality of treatments and/or therapeutic agents for the purpose of objectively identifying the best treatment or agent for the particular patient. The system includes the initial preparation of cohesive multicellular particulates of the tissue sample, rather than enzymatically dissociated cell suspensions or preparations, for initial tissue culture monolayer preparation. Practical monolayers of cells may thus be formed to enable meaningful screening of a plurality of treatments and/or agents. By subjecting uniform samples of cells to a wide variety of active agents (and concentrations thereof), the most promising agent and concentration for treatment of a particular patient can be determined. For assays concerning cancer treatment, a two-stage evaluation is contemplated in which both acute cytotoxic and longer term inhibitory effect of a given anti-cancer agent are investigated.

8 Claims, No Drawings

OTHER PUBLICATIONS

Cilley, R., et al., "Fetal Lung Development: Airway Pressure Enhances the Expression of Developmental Genes," Journal of Pediatric Surgery, vol. 35, No. 1, pp. 113–119 (2000).
Dietel, M., et al., "In Vitro Prediction of Cytostatic Drug Resistance in Primary Cell Cultures of Solid Malignant Tumours," Eur j Cancer, vol. 29A, No. 3, pp. 416–420 (1993).
Dudley, D., et al., "A Human Endometrial Explant System: Validation and Potential Applications," Am J Obstet Gynecol, vol. 167, No. 6, pp. 1774–1780 (1992).
Frykholm, G., et al., "Heterogeneity in Antigenic Expression and Radiosensitivity in Human Colon Carcinoma Cell Lines," In Vitro Cell Dev. Biol., vol. 27A, pp. 900–906 (1991).
Fulda, S., et al., "Antiproliferative Potential of Cytostatic Drugs on Neuroblastoma Cells In Vitro," Eur J of Cancer, vol. 31A, No. 4, pp. 616–621 (1995).
Gamboa, G., et al., "Characterization and Development of UCI 107, a Primary Human Ovarian Carcinoma Cell Line," Gynecologic Oncology, vol. 58, pp. 336–343 (1995).
Ghosh, A., et al., "Immunohistological Staining of Reactive Mesothelium Mesothelioma, and Lung Carcinoma with a Panel of Monoclonal Antibodies," J Clin Pathol, vol. 40, pp 19–25 (1987).
Goldsworthy, T., et al., "Concepts, Labeling Procedures, and Design of Cell Proliferation Studies Relating to Carcinogenesis," Environmental Health Perspectives, vol. 101, supp. 5, pp. 59–66 (1993).
Gress, T., et al., "Development of a Database on Transcribed Sequences in Tumour Cells and Identification of Changes in Transcription Patterns Related to Transformation and Other Tumour Cell Properties for the Global Finger Printing Analysis of Human Pancreatic Carcinoma cDNA Libraries," Biomed l. Health Res., vol. 24, pp. 171–181 (1998).
Hoffman, R., "The Three–Dimensional Question: Can Clinically Relevant Tumor Drug Resistance be Measured In Vitro?" Cancer and Metastasis Reviews, vol. 13, No. 2, pp. 169–173 (1994).
Kaaijk, P., et al., "Daunorubicin and Doxorubicin but not BCNU have Deleterious Effects on Organotypic Multicellular Spheroids of Gliomas," British Journal of Cancer, vol. 74, No. 2, pp. 187–193 (1996).
Kitamura, M., et al., "Chemosensitivty of Gastric Cancer Using Adhesive Tumor Cell Culture System," Oncology Reports, vol. 2, No. 1, pp. 27–31 (1995).
Kornblith, P., "Role of Tissue Culture in Prediction of Malignancy," Clinical Neurosurgery, vol. 25, pp. 346–376 (1978).*
Kornblith, P., et al., "Variations in Response of Human Brain Tumors to BCNU In Vitro," Journal of Neurosurgery, vol. 48, No. 4, pp. 580–586 (1978).*
Nance, K., et al., "Immunocytochemical Panel for the Identification of Malignant Cells in Serous Effusions," Am J Clin Pathol, vol. 95, pp. 867–874 (1991).*
Persons, D., et al., "Interphase Molecular Cytogenetic Analysis of Epithelial Ovarian Carcinomas," American Journal of Pathology, vol. 142, No. 3, pp. 733–741 (1993).*
Pinkus, G., et al., "Optimal Immunoreactivity of Keratin Proteins in Formalin–Fixed, Paraffin–Embedded Tissue Requires Preliminary Trypsinization," Journal of Histochemistry and Cytochemistry, vol. 33, No. 5, pp. 465–473 (1985).*

Raju, G., "The Histological and Immunohistochemical Evidence of Squamous Metaplasia from the Myoepithelial Cells in the Breast," Histopathology, vol. 17, No. 3, pp. 272–275 (1990).*
Singh, H., et al., "Significance of Epithelial Membrane Antigen in the Work–Up of Problematic Serous Effusions," Diagnostic Cytopathology, vol. 13, No. 1, pp. 3–7 (1995).*
Stephens, S., et al., "A Longitudinal Study of γ–Interferon Production by Peripheral Blood Mononuclear Cells from Breast– and Bottle–Fed Infants," Clin. Exp. Immunol., vol. 65, pp. 396–400 (1986).*
Stewart, R., et al., "Glutamate Accumulation By Human Gliomas and Meningiomas in Tissue Culture," Brain Research, vol. 118, No. 3, pp. 441–452 (1976).*
Stoop, J., et al., "Identification of Malignant Cells in Serous Effusins Using a Panel of Monoclonal Antibodies Ber–Ep4, MCA–b–12 and EMA," Cytopathology, vol. 3, pp. 297–302 (1992).*
Wiseman, I., "A Modification of Hepatest, using the Terasaki Plate, for the Detection of $Hb_sAg$ in Blood Donors," J Clin Pathol. vol. 29, No. 3, pp. 264–266 (1976).*
International Search Report for PCT/US01/32540 dated Apr. 18, 2002.*
International Search Report for PCT/US97/11595 dated Aug. 17, 1998.*
International Search Report for EP 97 93 3267 dated May 3, 2002.*
Alley, M., et al., "Morphometric and Colorimetric Analyses of Human Tumor Cell Line Growth and Drug Sensitivity in Soft Agar Culture," Cancer Research, vol. 51, pp. 1247–1256 (1991).
Andreotti, P., et al., "TCA–100 Tumour Chemosensitivity Assay: Differences in Sensitivity between Cultured Tumour Cell Lines and Clinical Studies," Journal of Bioluminescence and Chemiluminescence, vol. 9, pp. 373–378 (1994).
Arnold, J., et al., "Evaluation of Chemopreventative Agents in Different Mechanistic Classes Using a Rat Tracheal Epithelial Cell Culture Transformation Assay," Cancer Research, vol. 55, pp. 537–543 (1995).
Bosanquet, A., "Short–term In Vitro Drug Sensitivity Tests For Cancer Chemotherapy. A Summary of Correlations of Test Result With Both Patient Response and Survival," FORUM 4.2, pp. 179–195 (1994).
Fruehauf, J., "In Vitro Assay–assisted Treatment Selection For Women With Breast or Ovarian Cancer," Endocrine–Related Cancer, vol. 9, pp. 171–182 (2002).
Gerweek, et al., "Radiation Sensitivity of Cultured Human Glioblastoma Cells," Radiology, vol. 125, No. 1, pp. 231–234 (1977).*
Ghosh, A., et al., "Immunohistological Staining of Reactive Mesothelium, Mesothelioma, and Lung Carcinoma with a Panel of Monoclonal Antibodies," J. Clin. Pathol. vol. 40, pp 19–25 (1987).*
Kaaijk, P., et al., "Daunorubicin and Doxorubicin but not BCNU have Deleterious Effects on Organotypic Multicellular Spheroids of Gliomas," British Journal of Cancer, vol. 74, No. 2, pp. 187–193 (1996).*
Kruczynski, A., et al., "Evidence of a Direct Relationship Between the Increase in the In Vitro Passage Number of Human Non–Small–Cell–Lung Cancer Primocultures and their Chemosensitivity," Anticancer Research, vol. 13, pp. 507–514 (1993).*

McGuire, W., et al., "In vitro assays to Predict Drug Sensitivity and Drug Resistance, A Panel Discussion," Breast Cancer Research and Treatment, vol. 12, pp. 7–21 (1988).*

Robert, J., "Chemosensitivity Testing. Prediction of Response to Anticancer Drugs Using In Vitro Assays," Electronic Journal of Oncology, vol. 2, pp. 198–210 (1999).

Stoop, J., et al., "Identification of Malignant Cells in Serous Effusions Using a Panel of Monoclonal Antibodies Ber–EP4, MCA–b–12 and EMA," Cytopathology, vol. 3, pp. 297–302 (1992).

Freshney, R.I., *Culture of Animal Cells: A Manual of Basic Technique*, 2nd edition, pp. 107, 124–126, 179, 233–234, 290 (1987).

Guo et al., "Direct fluorescence analysis of genetic polymorphisms by hybridization with oligonucleotide arrays on glass supports," *Nucleic Acids Research* 22(24):5456–5465 (1994).

Pfost et al., "A SNPshot: pharmacogenetics and the future of drug therapy," *TIBTECH* 18:334–338 (Aug. 2000).

Stephens, J.C., "Single–nucleotide Polymorphisms, Haplotypes, and Their Relevance to Pharmacogenetics," *Molecular Diagnosis* 4(4):309–317 (1999).

Tannock et al., *The Basic Science of Oncology*, 2nd edition, pp. 247–248, 261–265, 303–306(1992).

Becton–Dickinson Catalog, Anti–Cytokeratin (CAM 5.2) Reagent, pp. 1–11 (1997).

Boehringer Mannheim Catalog, Anti–Cytokeratin AEI/AE3, (1996).

DAKO Catalog, Specification Sheet for Monoclonal Mouse Anti–Human Epithelial Membrane Antigen, pp. 1–2 (1996).

* cited by examiner

METHOD FOR PREPARING CELL CULTURES FROM BIOLOGICAL SPECIMENS FOR CHEMOTHERAPEUTIC AND OTHER ASSAYS

RELATED APPLICATION

This application is a continuation of U.S. application Ser. No. 08/679,056, filed Jul. 12, 1996 now U.S. Pat. No. 5,728,541.

FIELD OF THE INVENTION

The invention relates to screening and testing of active agents, including chemotherapeutic agents, to predict potential efficacy in individual patients in whom treatment with such agents is indicated.

INTRODUCTION

All active agents including chemotherapeutic active agents are subjected to rigorous testing as to efficacy and safety prior to approval for medical use in the United States. Methods of assessing efficacy have included elaborate investigations of large populations in double blind studies as to a given treatment method and/or active agent, with concomitant statistical interpretation of the resulting data, but these conclusions are inevitably generalized as to patient populations taken as a whole. In many pharmaceutical disciplines and particularly in the area of chemotherapy, however, the results of individual patient therapy may not comport with generalized data—to the detriment of the individual patient. The need has been long recognized for a method of assessing the therapeutic potential of active agents, including but not limited to chemotherapeutic agents, for their efficacy as to a given individual patient, prior to the treatment of that patient.

Prior art assays already exist which expose malignant tissue of various types to a plurality of active agents, for the purpose of assessing the best choice for therapeutic administration. For example, in Kruczynski, A., et al., "Evidence of a direct relationship between the increase in the in vitro passage number of human non-small-cell-lung cancer primocultures and their chemosensitivity," *Anticancer Research*, vol. 13, no. 2, pp. 507–513 (1993), chemosensitivity of non-small-cell-lung cancers was investigated in in vivo grafts, in in vitro primocultures and in commercially available long-term cancer cell lines. The increase in chemosensitivity was documented and correlated with morphological changes in the cells in question. Sometimes animal model malignant cells and/or established cell cultures are tested with prospective therapy agents, see for example Arnold, J. T., "Evaluation of chemopreventive agents in different mechanistic classes using a rat tracheal epithelial cell culture transformation assay," *Cancer Res.*, vol. 55, no. 3, pp. 537–543 (1995).

When actual patient cells are used to form in vitro assays focussed on individual patients, in typical prior art processes the cells are harvested (biopsied) and trypsinized (connective tissue digested with the enzyme trypsin) to yield a cell suspension suitable for conversion to the desired tissue culture form. The in vitro tissue culture cell collections which result from these techniques are generally plagued by their inability accurately to imitate the chemosensitivity of the original tumor or other cell biopsy. Standard cloning and tissue culture techniques are moreover excessively complicated and expensive for use in a patient-by-patient assay setting. A need thus remains for a technique of tissue culture preparation which provides cell cultures, for drug screening purposes, in which after simple preparation the cell cultures react in a manner equivalent to their in vivo reactivity, to enable drug or chemotherapeutic agent screening as to a particular patient for whom such screening is indicated.

SUMMARY OF THE INVENTION

In order to meet this need, the present invention is an improved system for screening a multiple of candidate therapeutic or chemotherapeutic agents for efficacy as to a specific patient, in which a tissue sample from the patient is harvested, cultured and separately exposed to a plurality of treatments and/or therapeutic agents for, the purpose of objectively identifying the best treatment for the cultured cells obtained from the patient. Specific method innovations such as tissue sample preparation techniques render this method practically as well as theoretically useful. One particularly important tissue sample preparation technique is the initial preparation of cohesive multicellular particulates of the tissue sample, rather than enzymatically dissociated cell suspensions or preparations, for initial tissue culture monolayer preparation. With respect to the culturing of malignant cells, for example, it is believed (without any intention of being bound by the theory) that by maintaining the malignant cells within a multicellular particulate of the originating tissue, growth of the malignant cells themselves is facilitated versus the overgrowth of fibroblasts or other cells which tends to occur when suspended tumor cells are grown in culture. Practical monolayers of cells may thus be formed to enable meaningful screening of a plurality of treatments and/or agents. Growth of cells is monitored to ascertain the time to initiate the assay and to determine the growth rate of the cultured cells; sequence and timing of drug addition is also monitored and optimized. By subjecting uniform samples of cells to a wide variety of active agents (and concentrations thereof), the most efficacious agent can be determined. For assays concerning cancer treatment, a two-stage evaluation is contemplated in which both acute cytotoxic and longer term inhibitory effect of a given anti-cancer agent are investigated.

DETAILED DESCRIPTION OF THE INVENTION

The present invention is a system for screening a multiple of candidate therapeutic or chemotherapeutic agents for efficacy as to a specific patient, in which a tissue sample from the patient is harvested and separately exposed to a plurality of treatments and/or therapeutic agents for the purpose of objectively identifying the best treatment or agent. Specific method innovations such as tissue sample preparation techniques render this method practically as well as theoretically useful. One particularly important tissue sample preparation technique is the initial preparation of cohesive multicellular particulates (explants) of the tissue sample, rather than enzymatically dissociated cell suspensions or preparations, for initial tissue culture monolayer preparation. Cell growth, and sequence and timing of drug addition, are monitored and optimized.

An important application of the present invention is the screening of chemotherapeutic agents and other antineoplastic therapies against tissue culture preparations of malignant cells from the patients from whom malignant samples are biopsied. Related anti-cancer therapies which can be screened using the inventive system are both radiation therapy and agents which enhance the cytotoxicity of radiation, as well as immunotherapeutic anti-cancer agents.

Screening processes for treatments or therapeutic agents for nonmalignant syndromes are also embraced within this invention, however, and include without limitation agents which combat hyperproliferative syndromes, such as psoriasis, or wound healing agents. Nor is the present efficacy assay limited only to the screening of active agents which speed up (healing) or slow down (anti-cancer, anti-hyperproliferative) cell growth because agents intended to enhance or to subdue intracellular biochemical functions may be tested in the present tissue culture system also. For example, the formation, or blocking of enzymes, neurotransmitters and other biochemicals may be screened with the present assay methods prior to treatment of the patient.

When the patient is to be treated for the presence of tumor, in the preferred embodiment of the present invention a tumor biopsy of >100 mg of non-necrotic, non-contaminated tissue is harvested from the patient by any suitable biopsy or surgical procedure known in the art. Biopsy sample preparation generally proceeds as follows under a Laminar Flow Hood which should be turned on at least 20 minutes before use. Reagent grade ethanol is used to wipe down the surface of the hood prior to beginning the sample preparation. The tumor is then removed, under sterile conditions, from the shipping container and is minced with sterile scissors. If the specimen arrives already minced, the individual tumor pieces should be divided into four groups. Using sterile forceps, each undivided tissue quarter is then placed in 3 ml sterile growth medium (Standard F-10 medium containing 17% calf serum and a standard amount of Penicillin and Streptomycin) and systematically minced by using two sterile scalpels in a scissor-like motion, or mechanically equivalent manual or automated opposing incisor blades. This cross-cutting motion is important because the technique creates smooth cut edges on the resulting tumor multicellular particulates. Preferably but not necessarily, the tumor particulates each measure 1 $mm^3$. After each tumor quarter has been minced, the particles are plated in culture flasks using sterile pasteur pipettes (9 explants per T-25 or 20 particulates per T-75 flask). Each flask is then labelled with the patient's code, the date of explantation and any other distinguishing data. The explants should be evenly distributed across the bottom surface of the flask, with initial inverted incubation in a 37° C. incubator for 5–10 minutes, followed by addition of about 5–10 ml sterile growth medium and further incubation in the normal, non-inverted position. Flasks are placed in a 35° C., non-$CO_2$ incubator. Flasks should be checked daily for growth and contamination. Over a period of a few weeks, with weekly removal and replacement of 5 ml of growth medium, the explants will foster growth of cells into a monolayer. With respect to the culturing of malignant cells, it is believed (without any intention of being bound by the theory) that by maintaining the malignant cells within a multicellular particulate of the originating tissue, growth of the malignant cells themselves is facilitated versus the overgrowth of fibroblasts (or other unwanted cells) which tends to occur when suspended tumor cells are grown in culture.

The use of the above procedure to form a cell monolayer culture maximizes the growth of malignant cells from the tissue sample, and thus optimizes ensuing tissue culture assay of chemotherapeutic action of various agents to be tested. Enhanced growth of actual malignant cells is only one aspect of the present invention, however; another important feature is the growth rate monitoring system used to oversee growth of the monolayer once formed. Once a primary culture and its derived secondary monolayer tissue culture has been initiated, the growth of the cells is monitored to ascertain the time to initiate the chemotherapy assay and to determine the growth rate of the cultured cells.

Monitoring of the growth of cells is conducted by counting the cells in the monolayer on a periodic basis, without killing or staining the cells and without removing any cells from the culture flask. The counting may be done visually or by automated methods, either with or without the use of estimating techniques known in the art (counting in a representative area of a grid multiplied by number of grid areas, for example). Data from periodic counting is then used to determine growth rates which may or may not be considered parallel to growth rates of the same cells in vivo in the patient. If growth rate cycles can be documented, for example, then dosing of certain active agents can be customized for the patient. The same growth rate can be used to evaluate radiation treatment periodicity, as well. It should be noted that with the growth rate determinations conducted while the monolayers grow in their flasks, the present method requires no hemocytometry, flow cytometry or use of microscope slides and staining, with all their concommitant labor and cost.

Protocols for monolayer growth rate generally use a phase-contrast inverted microscope to examine culture flasks incubated in a 37° C. (5% $CO_2$) incubator. When the flask is placed under the phase-contrast inverted microscope, ten fields (areas on a grid inherent to: the flask) are examined using the 10× objective, with the proviso that the ten fields should be non-contiguous, or significantly removed from one another, so that the ten fields are a representative sampling of the whole flask. Percentage cell occupancy for each field examined is noted, and averaging of these percentages then provides an estimate of overall percent confluency in the cell culture. When patient samples have been divided between two or among three or more flasks, an average cell count for the total patient sample should be calculated. The calculated average percent confluency should be entered into a process log to enable compilation of data—and plotting of growth curves—over time. Monolayer cultures may be photographed to document cell morphology and culture growth patterns.

The applicable formula is:

$$\text{Percent confluency} = \frac{\text{estimate of the area occupied by cells}}{\text{total area in an observed field}}$$

As an example, therefore, if the estimate of area occupied by the cells is 30% and the total area of the field is 100%, percent confluency is 30/100, or 30.

Adaptation of the above protocol for non-tumor cells is straightforward and generally constitutes an equivalent procedure.

Active agent screening using the cultured cells does not proceed in the initial incubation flask, but generally proceeds using plates such as microtiter plates. The performance of the chemosensitivity assay used for screening purposes depends on the ability to deliver a reproducible cell number to each row in a plate and/or a series of plates, as well as the ability to achieve an even distribution of cells throughout a given well. The following procedure assures that cells are reproducibly transferred from flask to microtiter plates, and cells are evenly distributed across the surface of each well.

The first step in preparing the microtiter plates is, of course, preparing and monitoring the monolayer as described above. The following protocol is exemplary and susceptible of variation as will be apparent to one skilled in the art. Cells are removed from the culture flask and a cell pellet is prepared by centrifugation. The cell pellet derived from the monolayer is then suspended in 5 ml of the growth medium and mixed in a conical tube with a vortex for 6 to 10 seconds. The tube is then rocked back and forth 10 times. A 36 μl droplet from the center of the conical tube is pipetted onto one well of a 96 well plate. A fresh pipette is then used to pipette a 36 μl aliquot of trypan blue solution, which is added to the same well, and the two droplets are mixed with repeated pipette aspiration. The resulting admixture is then divided between two hemocytometer chambers for examination using a standard light microscope. Cells are counted in two out of four hemocytometer quadrants, under 10× magnification. Only those cells which have not taken up the trypan blue dye are counted. This process is repeated for the second counting chamber. An average cell count per chamber is thus determined. Using means known in the art, the quadrant count values are checked, logged, multiplied by $10^4$ to give cells/ml, and the total amount of fluid (growth medium) necessary to suspend remaining cell aliquots is calculated accordingly.

After the desired concentration of cells in medium has been determined, additional cell aliquots from the monolayer are suspended in growth medium via vortex and rocking and loaded into a Terasaki dispenser known in the art. Aliquots of the prepared cell suspension are delivered into the microtiter plates using Terasaki dispenser techniques known in the art. A plurality of plates may be prepared from a single cell suspension as needed. Plates are then wrapped in sterile wet cotton gauze and incubated in an incubator box by means known in the art.

After the microtiter plates have been prepared, exposure of the cells therein to active agent is conducted according to the following exemplary protocol. During this portion of the inventive assay, the appropriate amount of specific active agent is tranferred into the microtiter plates prepared as described above. A general protocol, which may be adapted, follows. Each microtiter plate is unwrapped from its wet cotton gauze sponge and microscopically examined for cell adhesion. Control solution is dispensed into delineated rows of wells within the grid in the microtiter plate, and appropriate aliquots of active agent to be tested are added to the remaining wells in the remaining rows. Ordinarily, sequentially increasing concentrations of the active agent being tested are administered into progressively higher numbered rows in the plate. The plates are then rewrapped in their gauze and incubated in an incubator box at 37° C. under 5% $CO_2$. After a predefined exposure time, the plates are unwrapped, blotted with sterile gauze to remove the agent, washed with Hank's Balance Salt Solution, flooded with growth medium, and replaced in the incubator in an incubator box for a predefined time period, after which the plates may be fixed and stained for evaluation.

Fixing and staining may be conducted according to a number of suitable procedures; the following is representative. After removal of the plates from the incubator box, culture medium is poured off and the plates are flooded with Hank's Balance Salt Solution. After repeated flooding (with agitation each time) the plates are then flooded with reagent grade ethanol for 2–5 minutes. The ethanol is then poured off. Staining is accomplished with approximately 5 ml of Giemsa Stain per plate, although volume is not critical and flooding is the goal. Giemsa stain should be left in place 5 min. ±30 seconds as timing influences staining intensity. The Giemsa stain is then poured off and the plates are dipped 3 times cold tap water in a beaker. The plates are then inverted, shaken vigorously, and air dried overnight (with plate lids off) on a rack on a laboratory bench. Cells per well are then counted manually or by automated and/or computerized means, to derive data regarding chemosensitivity of cells at various concentrations of exposure. One particularly useful computer operating environment for counting cells is the commercially available OPTIMATE compiler, which is designed to permit an optical counting function well suited to computerized cell counting procedures and subsequent calculations.

The above procedures do not change appreciably when cell growth promoters are assayed rather than cell arresting agents such as chemotherapeutic agents. The present assay allows cell death or cell growth to, be monitored with equal ease. In any case, optimization of use of the present system will involve the comparative testing of a variety of candidate active agents, for selection of the best candidate for patient treatment based upon the in vitro results. One particularly advantageous embodiment of the above described invention comprises a two-stage assay for cytotoxicity followed by evaluation of longer-term inhibitory effect. Chemotherapeutic agents may thus be evaluated separately for both their direct chemotherapeutic effect as well as for their longer duration efficacy.

Identification of one or more active agents or chemotherapeutic agents is peripheral to the present invention, which is intended for the efficacy screening of any or all of them as to a given patient. Literally any active agent may be screened according to the present invention; listing exemplary active agents is thus omitted here.

The essence of the invention thus includes the important feature of the simplicity of the present system—cohesive multicellular particulates of the patient tissue to be tested are used to form cell monolayers; growth of those monolayers is monitored for accurate prediction of correlating growth of the same cells in vivo; and differing concentrations of a number of active agents may be tested for the purpose of determining not only the most appropriate agent but the most appropriate concentration of that agent for actual patient exposure (according to the calculated cell growth rates). It is also important to note, in the context of the invention, that the present system allows in vitro tests to be conducted in suspensions of tissue culture monolayers grown in nutrient medium under fast conditions (a matter of weeks), rather than with single cell progeny produced by dilution cloning over long periods of time. In some cases, the present invention is a two stage assay for both cytotoxicity and the longer-term growth inhibitory.

Although the present invention has been described with respect to specific materials and methods above, the invention is only to be considered limited insofar as is set forth in the accompanying claims.

I claim:

1. A method for preparing a biopsy sample of tissue containing malignant cells for chemosensitivity testing, comprising:

(a) obtaining a tumor specimen from a biopsy sample of tissue containing malignant cells;

(b) mechanically separating said specimen into cohesive multicellular particulates having smooth cut edges;

(c) growing a tissue culture monolayer from said cohesive multicellular particulates having smooth cut edges;

(d) inoculating cells from said monolayer into a plurality of segregated sites;

(e) treating said plurality of sites with at least one agent; and (f) assessing chemosensitivity of the cells in said plurality of sites.

2. The method according to claim 1 wherein said plurality of segregated sites comprise a plate containing a plurality of wells therein.

3. The method according to claim 2 wherein said plurality of wells is treated over a length of timed adequate to permit assessment of both initial cytotoxic effect and longer term inhibitory effect of at least one of said plurality of active agents.

4. The method according to claim 3 wherein step (d) is accomplished by a multiple well pipetting device.

5. The method according to claim 4 wherein the cells in step (d) are further suspended in medium prior to inoculation into said plate containing a plurality of wells therein.

6. The method according to claim 1 wherein said agent is at least one of the agents selected from the group consisting of a radiation therapy agent, a radiation therapy sensitizing agent and a radiation therapy desensitizing agent.

7. The method according to claim 1 wherein said agent is an immunotherapeutic agent.

8. A method for preparing a biopsy sample of tissue containing malignant cells for chemosensitivity testing, comprising:

(a) obtaining a tumor specimen from a biopsy sample of tissue containing malignant cells;

(b) mechanically separating said specimen into cohesive multicellular particulates of minced tumor tissue;

(c) growing a tissue culture monolayer from said cohesive multicellular particulates of minced tumor tissue;

(d) inoculating cells from said monolayer into a plurality of segregated sites;

(e) treating said plurality of sites with at least one agent; and (f) assessing chemosensitivity of the cells in said plurality of sites.

* * * * *